United States Patent [19]

Saito

[11] Patent Number: 5,090,400
[45] Date of Patent: Feb. 25, 1992

[54] MEASURING ENDOSCOPE

[75] Inventor: Satoshi Saito, Tochigi, Japan

[73] Assignee: Kabushiki Kaisha Toshiba, Kawasaki, Japan

[21] Appl. No.: 625,094

[22] Filed: Dec. 10, 1990

Related U.S. Application Data

[62] Division of Ser. No. 176,006, Mar. 31, 1988, Pat. No. 4,986,262.

[30] Foreign Application Priority Data

| Mar. 31, 1987 | [JP] | Japan | 62-76494 |
| Apr. 30, 1987 | [JP] | Japan | 62-106921 |
| Aug. 20, 1987 | [JP] | Japan | 62-205051 |

[51] Int. Cl.$^5$ .............................................. A61B 1/04
[52] U.S. Cl. .......................................... 128/6; 358/98; 356/2
[58] Field of Search ............................ 128/6, 664, 774; 350/162.17, 162.2; 356/2, 305; 358/98

[56] References Cited

U.S. PATENT DOCUMENTS

| 4,093,346 | 6/1978 | Nishino et al. | 350/162.2 |
| 4,588,294 | 5/1986 | Siegmund | 128/6 |
| 4,637,715 | 1/1987 | Idesawa | 356/2 |
| 4,834,070 | 5/1989 | Saitou | 128/6 |
| 4,986,262 | 1/1991 | Saito | 128/6 |

FOREIGN PATENT DOCUMENTS 293222 12/1987 Japan .............................. 350/162.17

OTHER PUBLICATIONS

Yamaguchi et al., *Gastroenterological Endoscopy*, vol. (25)6, pp. 868-875, Jun. 1983.

Primary Examiner—Stephen C. Pellegrino
Assistant Examiner—Ralph A. Lewis
Attorney, Agent, or Firm—Foley & Lardner

[57] ABSTRACT

An endoscope is presented which enables one to carry out measurement of an unevenness existing on an object by the use of laser beams, without being affected by white light for observation. White light is irradiated on the object only during the time when measurement of the unevenness is not being carried out, and the image information obtained by the use of the white light is displayed continuously while being stored in a memory.

8 Claims, 13 Drawing Sheets

FIG.9
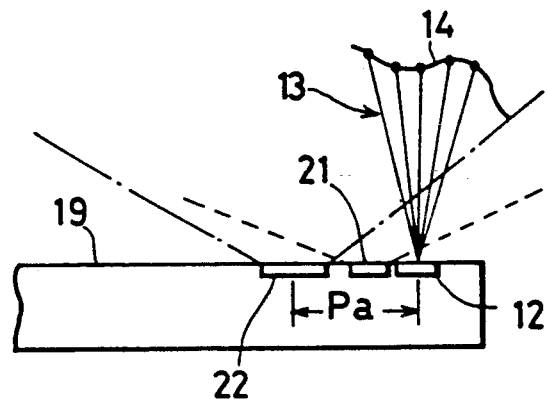
FIG.10
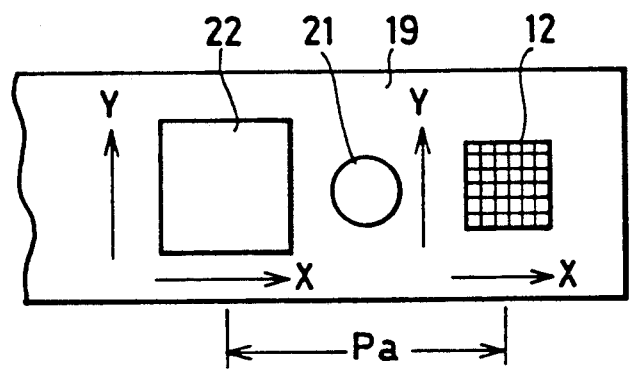
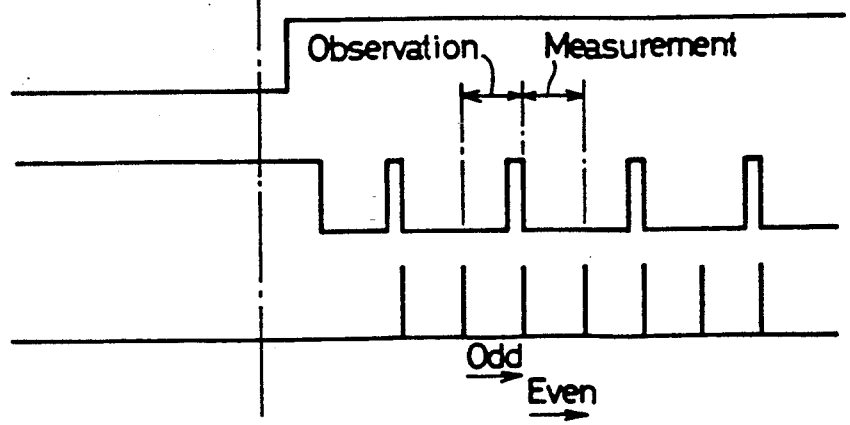

FIG.15
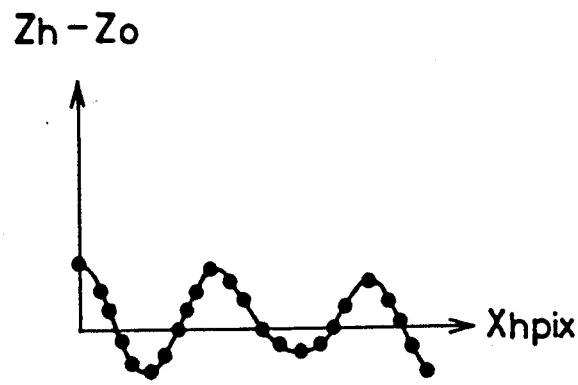
FIG.16
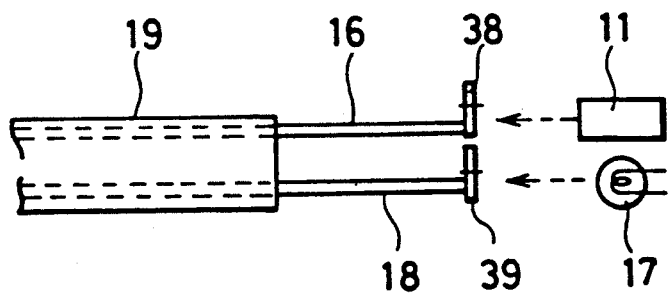
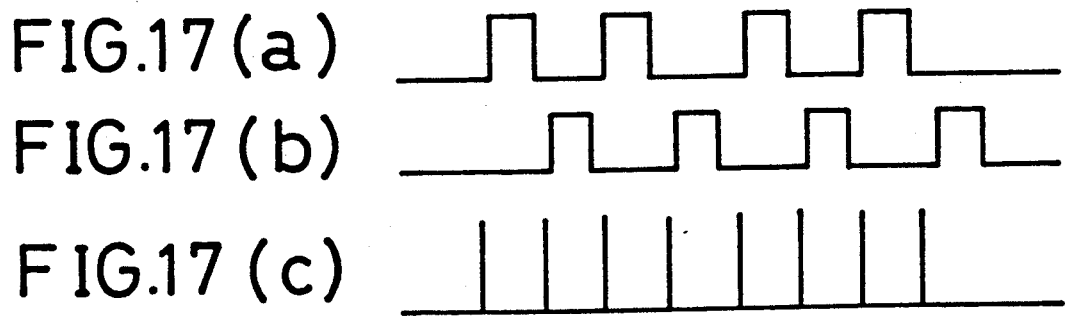
FIG.17(a)
FIG.17(b)
FIG.17(c)

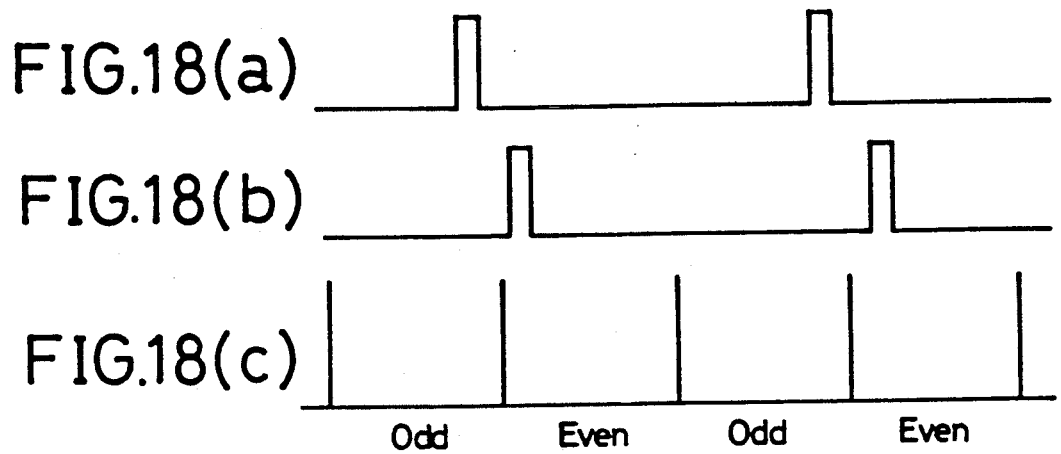
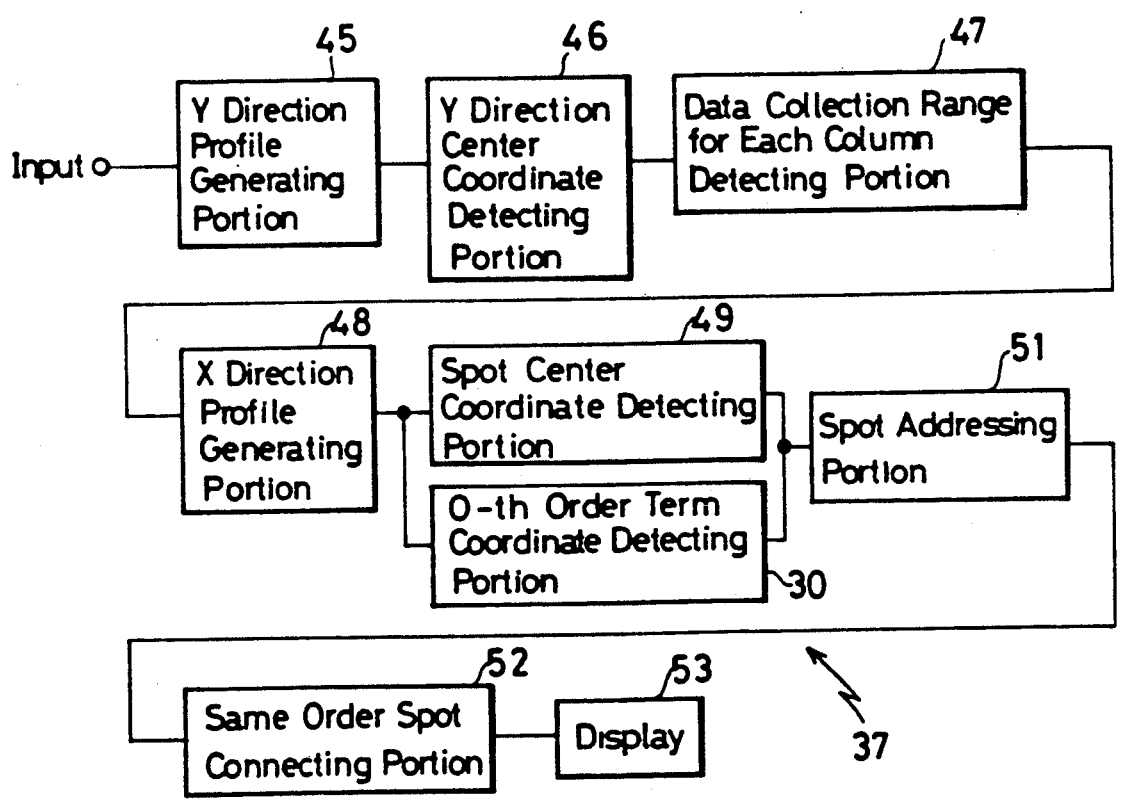

MEASURING ENDOSCOPE

This application is a division of application Ser. No. 07/176,006, filed Mar. 31, 1988, now U.S. Pat. No. 4,986,262.

BACKGROUND OF THE INVENTION

The present invention relates to a measuring endoscope which enables one to measure the size of a morbid growth or the like within the body.

As a typical conventional apparatus for measuring the size of a morbid growth or the like within the body by means of an endoscope, there is known an apparatus, for example, which makes use of a device as shown in FIG. 1 through FIG. 4 (Gastroenterological Endoscopy, Vol. (25) 6, June, 1983, P. 868).

In FIG. 1, the endoscope apparatus has a laser light source 11 and a transmission type fiber diffraction grating 12; transmission type fiber diffraction grating 12 constituted by combining two sheets of a planar array of glass fibers so that the fiber bundles on one plane cross perpendicularly to those on the other plane. Since about 100 or more glass fibers each with, for example, a diameter of 25 $\mu$m are arrayed close to each other to form a square, the transmission type fiber diffraction grating 12 has sides with dimensions of about 2.5 mm, which is quite adequate for mounting on the tip of a scope.

When laser beams from the laser light source 11 are incident at right angles on the transmission type fiber diffraction grating 12, a pattern projection light 13 is obtained as a two-dimensional spot like diffracted light arranged in matrix form. Projection of this light on a plane parallel to the transmission type diffraction grating 12 produces a two-dimensional matrix-like spot light pattern.

FIG. 2 shows the projected image of a spot light pattern when pattern projection light 13 is projected on a tilted screen from down below and viewed from above, at a location a prescribed distance away from the transmission type fiber diffraction grating 12. From the figure, there can be observed a phenomenon in which the interval between the spots increases in proportion to the distance away from the transmission type fiber diffraction grating, and, also, this increases as one moves towards the upper portion of FIG. 2.

In the conventional technique, the apparatus is so arranged as to measure the distance from an observation point to an object to be observed where a morbid growth or the like exists, as well as to measure the size and the degree of swelling or depression of the object.

FIG. 3 illustrates the situation where it becomes possible to measure the size of a morbid growth in an object to be measured 14 by generating changes in the interval between the spot lights projected on the object to be measured 14 in response to the form of the object to be measured 14, while giving a predetermined separation between the point of installation G of the transmission type fiber diffraction grating and a point of observation A, which is the point of installation of an object lens, image receiving element, or the like.

Now, in a measuring endoscope as in the above, there is generally arranged a source of white light which emits illumination light for observation, to provide a function for carrying out ordinary observation in addition to measurement.

However, if an illumination light for observation is incident on a living body or the like which is an object to be measured, simultaneous with the pattern projection light, halation is generated due to reflected light, as shown in FIG. 4. This leads to problems which make precise measurements difficult, such as the misrecognition of spots produced by the pattern projection light and the difficulty in the detection of spots because of the high background light levels resulting from background light due to the illumination for observation.

In addition, in the first example of the prior art described above, the glass fibers 12a and 12b with equal diameter, and hence producing an identical diffraction angle, are employed for the two sheets of one-dimensional fiber diffraction gratings, which together constitute a two-dimensional transmission type fiber diffraction grating 12, as shown in FIG. 5. This results in disadvantages in that detailed observation is difficult to make due to the observation points being distributed discretely as shown in FIG. 3, and that information on the unevenness of the object is visually more difficult to recognize.

FIG. 6 and FIG. 7 illustrate a second example of the prior art which compensates for the difficulties mentioned above.

In the second example of the prior art, it is attempted to recognize the unevenness by projecting a pinstripe pattern as shown in FIG. 7 on an object to be inspected, using a projection grating or reflection grating as shown in FIG. 6.

However, in the second example of the prior art, use is made only of light which either transmits through, or is reflected from, a part of the diffraction grating, so that the pinstripe pattern darkens due to reduction in the quantity of the pattern projection light, making it difficult to visualize the image.

To summarize, in the first example of the prior art, diffraction angles of the two sheets of one-dimensional fiber diffraction gratings, which together form a two-dimensional transmission type fiber diffraction grating, become identical so that detailed continuous measurement is difficult to realize due to discreteness of the points where measurement is to be made, leading to a problem in that unevenness information is visually more difficult to recognize.

On the other hand, in the second example of the prior art which was proposed to compensate for the difficulty in the first example, use is made only of light transmitted through or reflected from a portion of the grating, so the pinstripe pattern becomes dark due to a reduction in the quantity of the pattern projection light, resulting that the image is not easy to recognize.

SUMMARY OF THE INVENTION

It is an object of the present invention to provide an endoscope which enables one to obtain an exact measurement of the unevenness of an object to be measured It is another object of the present invention to provide an endoscope which enables one to measure the unevenness of an object to be observed without being affected by the white light that is used for irradiating the object for observation.

It is still another object of the present invention to provide an endoscope which enables one to carry out an exact measurement of the unevenness of an object to be measured simultaneous with the observation.

It is still another object of the present invention to provide an endoscope which enables one to easily obtain a visual depiction of the unevenness of an object to be measured.

According to one aspect of the present invention, irradiation timings for the pattern projection light for measurement and the illumination light for observation are controlled by an illumination timing control means, wherein there is obtained a distinct matrix-like two-dimensional spot light pattern on the object to be measured by removing the influence of the illumination light for observation.

Then, the spot light pattern projected on the object to be measured is picked up by an image receiving means, and, by an appropriate processing of the received image, exact measurements are taken of the distance between the image pickup means and the object to be measured, the size and the degree of swelling or depression of the object, and other such properties.

On the other hand, ordinary observation by the illumination light for observation can be performed without being adversely affected in particular by the irradiation of the pattern projection light.

In this way, measurement and ordinary observation can be performed appropriately.

According to another aspect of the invention, the laser light can be diffracted one-dimensionally in either the row or column direction by means of a one-dimensional fiber diffraction grating which constitutes a two-dimensional transmission type diffraction grating. This diffracted light is then diffracted again or enlarged two-dimensionally in the other (row or column) direction by means of another one-dimensional fiber diffraction grating or by a lens body that has a diffraction angle different from that of the one-dimensional fiber diffraction grating mentioned above. In this manner, in the two-dimensional spot light, the intervals between spots in the row or column direction are shortened or connected. The two-dimensional spot light pattern, projected on an object to be inspected, is converted to a pattern which approximates a pinstripe pattern, or converted to a pinstripe pattern.

According to still another aspect of the invention, on the distal end of the scope there are mounted a transmission type diffraction grating and an image receiving means with a predetermined interval that will generate a parallax only in the direction which is the same as the row direction of the spot light pattern that is projected. Light beams from a light source are diffracted by the transmission type diffraction grating to produce a matrix-like two-dimensional projected spot light pattern on the object to be inspected, and this projected image is picked up by the image receiving means. The image of the spot light pattern has intervals between spots for each column which vary according to the form of the object to be measured. The center coordinate of each column in the spot light pattern which is picked up is detected by a column direction center coordinate detection means, and then spot coordinate and order of diffraction are determined by a spot coordinate detection means for spots in each column whose center coordinate is determined as above. Next, spots with the same diffraction order in the respective columns are interpolated and joined by continuous line segments, and are converted to a pinstripe pattern to be displayed distinctly on a monitor or some type of visual display. From this pinstripe pattern it becomes possible to recognize the unevenness or the like existing on the object to be inspected.

These and other objects, features and advantages of the present invention will be more apparent from the following description of the preferred embodiments, taken in conjunction with the accompanying drawings.

BRIEF DESCRIPTION OF THE DRAWINGS

FIG. 9 and FIG. 10 are a side elevation and a plan view, respectively, of the distal end portion of the scope of the measuring endoscope, in accordance with the present invention;

FIG. 11 is a timing chart showing an example of irradiation timings of pattern projection light and an illumination light for the measuring endoscope in accordance with the present invention;

FIG. 15 is a characteristic diagram showing an example of a curve for displaced quantity formed in a pixel coordinate detecting portion;

FIG. 16 is a diagram of an irradiation timing control showing another embodiment of the present invention;

FIG. 17 is a timing chart showing an example of the irradiation timings for the pattern projection light and illumination light for observation by the embodiment shown in FIG. 16;

FIG. 18 is a timing chart showing a modified example of the irradiation timings for the pattern projection light and illumination light for observation by the embodiment shown in FIG. 16;

FIG. 19 is a block diagram showing the pixel coordinate detecting portion of the measuring endoscope in accordance with the present invention;

DETAILED DESCRIPTION OF THE PREFERRED EMBODIMENTS

Figure 1:
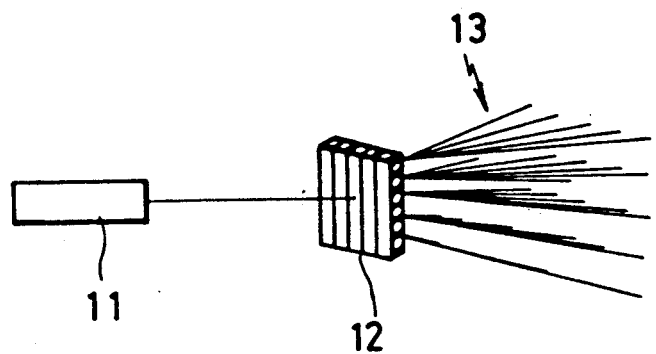
FIG. 1 is a diagram showing light beams diffracted by a conventional transmission type fiber diffraction grating.
Figure 2:
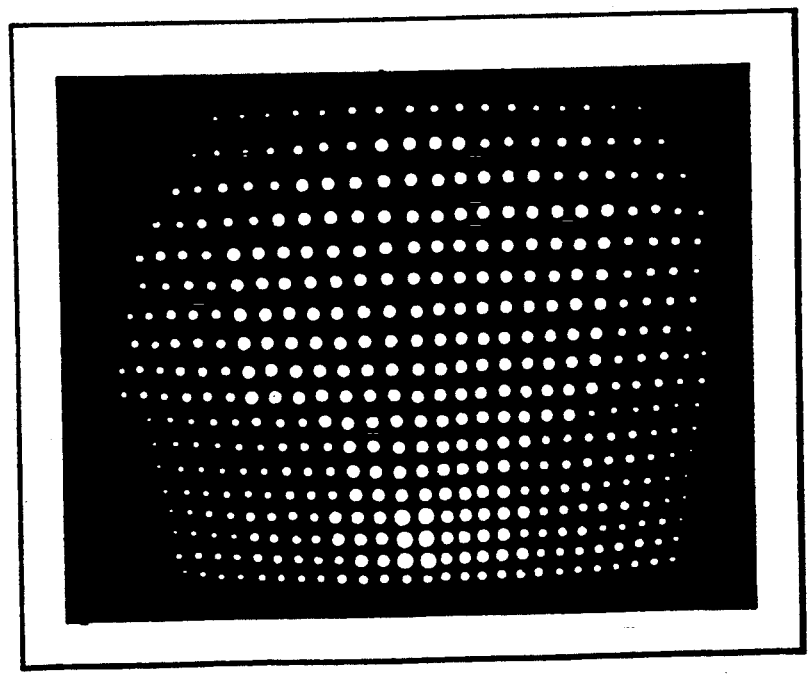
FIG. 2 is a picture showing a typical projected image of a spot light pattern obtained by the diffracted light beams shown in FIG. 1.
Figure 3:
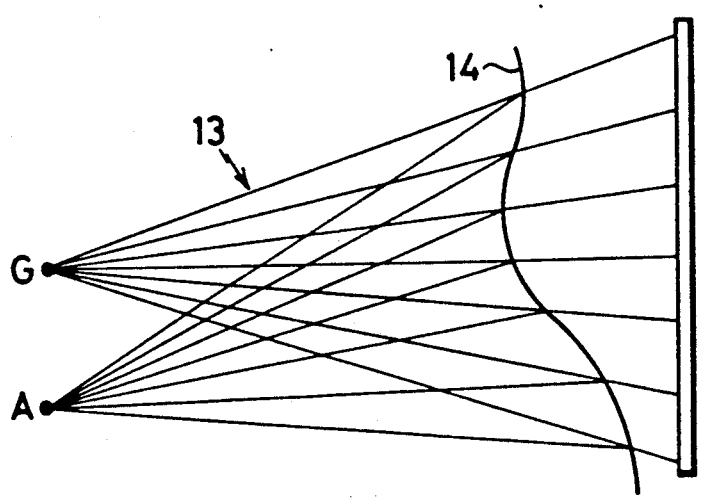
FIG. 3 is a diagram showing an observation on an object to be measured by the use of the transmission type fiber diffraction grating.
Figure 4:
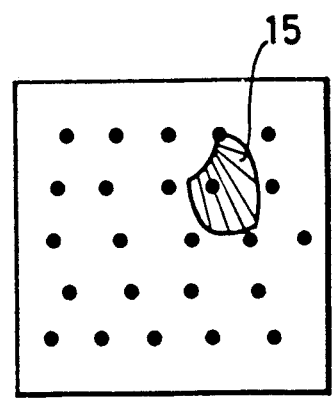
FIG. 4 is a diagram showing the state in which there is generated a halation in the spot light pattern due to reflected light of illumination light for observation.
Figure 5:
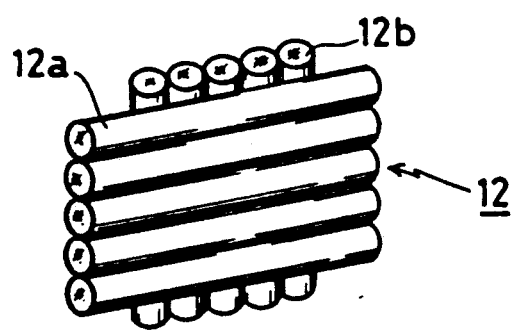
FIG. 5 is an enlarged perspective view of the transmission type fiber diffraction grating.
Figure 6:
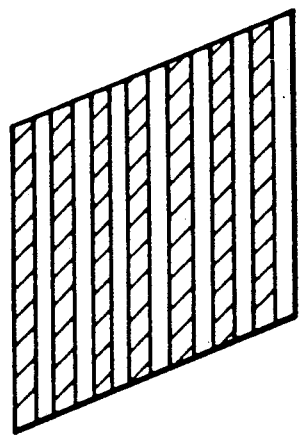
FIG. 6 is a perspective view of a reflection grating which is a second example of prior art.
Figure 7:
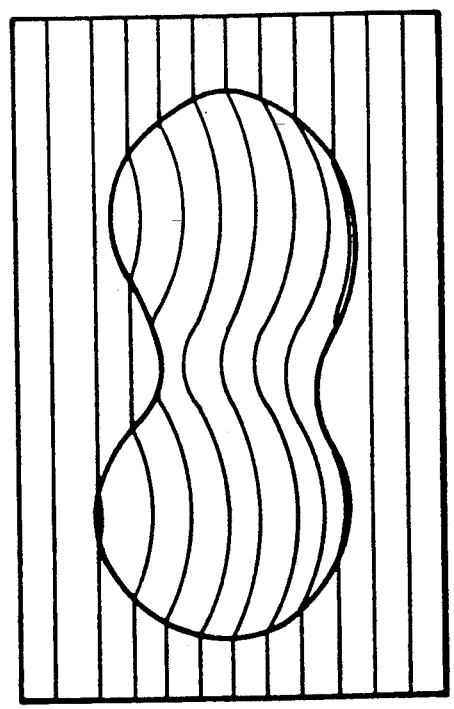
FIG. 7 is a picture showing a projected example of pinstripe pattern obtained by the reflection grating in the above.

FIG. 8 through FIG. 15 show an embodiment of the present invention;

In these figures, instruments, members, and other items that are identical or otherwise equivalent to those in FIG. 1 are given identical symbols to omit repeated descriptions thereof.

Figure 8:
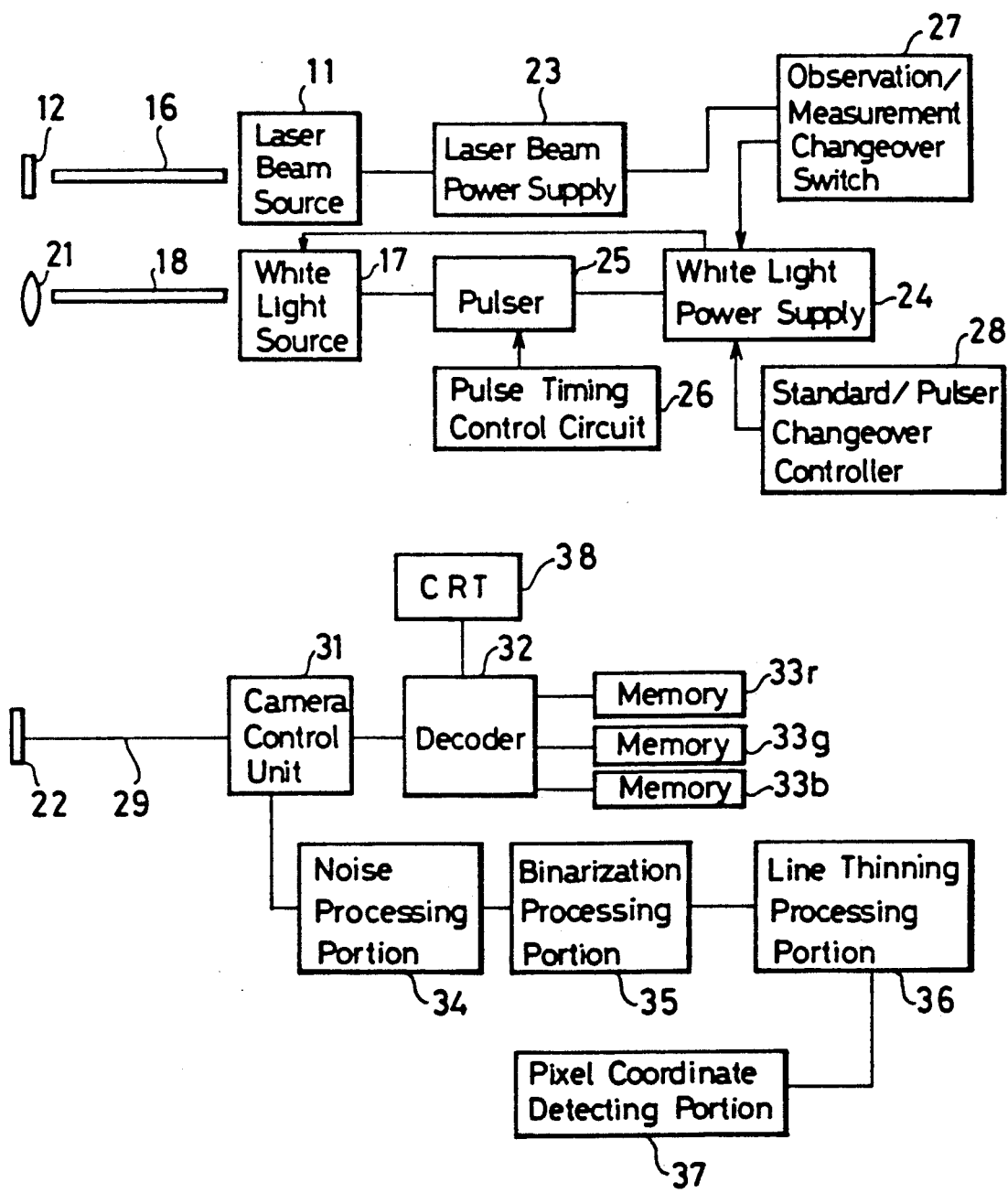
FIG. 8 are block diagrams showing the overall constitution of a measuring endoscope in accordance with the present invention.

Referring to FIG. 8 through FIG. 10, the measuring endoscope has an optical fiber 16 for guiding laser beams from a laser light source 11 and an optical fiber 18 for guiding illumination light for observation from a white light source 17. A scope 19, to be inserted into a body cavity, is constructed by integrally bundling both the optical fibers 16 and 18, the signal line connected to a solid-state image receiving element, and so on.

On the exit end of the optical fiber 16 which guides laser beams, namely, on the distal end of the scope, there is mounted a transmission type fiber diffraction grating 12, and on the exit end side of the optical fiber 18 which guides the illumination light for observation there is mounted an illumination lens 21, which works as an illumination means for supplying illumination light for observation. Reference numeral 22 signifies a solid-state image receiving element comprising a charge coupled device (CCD), where the solid-state image receiving element 22 may, for example, be a CCD itself, and is mounted on the scope with a prescribed interval $P_a$ corresponding to the parallax away from the transmission type fiber diffraction grating 12, as shown in FIG. 10. The transmission type fiber diffraction grating 12, the illumination lens 21 and the solid-state image receiving element 22 are disposed on the side of the scope 19 in the distal end of the scope, so that the endoscope in the present invention constitutes what is called the side-view type. Here, a CCD 22 and the grating 12 are arranged side by side in the X direction with their Y-axes aligned, and the parallax as seen from CCD 22 between spots of light beams which pass through grating 12 is restricted to be generated in the X direction only.

Further, 23 is a power supply for laser beams and 24 is a power supply for white light, and both power supplies 23 and 24 are connected respectively to the following instruments which constitute an irradiation timing control means. Namely, first, a pulser 25 is connected between the white light source 17 and the power supply 24, and a pulse timing control circuit 26 which controls the timings of the pulser 25 is connected to the pulser 25. Moreover, changeover signal lines of an observation/measurement changeover switch 27 are connected respectively to the power supplies 23 and 24 for laser beams and white light, and a standard/pulser changeover controller 28 is connected to the white light power supply 24.

On the other hand, a camera control unit 31 is connected to a signal line 29 of the solid-state image receiving element 22, and on the side of a television signal output line of the camera control unit 31 there are connected successively a decoder 32 and memories $33r$, $33g$, and $33b$ for storing signals for respective color components. Image pickup information processed in the decoder 32 is displayed on a CRT monitor 38. A luminance signal output line is connected separately to the camera control unit 31 to process spot light patterns, and a binarization processing portion 34, a noise processing portion 35, a line thinning processing portion 36 and a pixel coordinate detecting portion 37 are connected successively to the luminance signal output line.

Next, referring to FIG. 11 through FIG. 16, the operation of the system will now be described. FIG. 11(a) shows an ON/OFF state of the laser beam source 11, FIG. 11(b) shows an ON/OFF state of the white light source 17, and FIG. 11(c) shows the generation of timing blocks.

First, the control of illumination timings will be described. When the scope 19 is inserted into a desired site within the body, the observation/measurement changeover switch 27 is switched to the observation mode, and the standard mode is selected by the standard/pulser changeover controller 28; the endoscope being set to the standard mode in the ordinary observation mode. A constant voltage is supplied to the white light source 17 from the white light power supply 24 and illumination light for observation illuminates continuously an object to be measured (standard mode of FIG. 11(b)).

Further, if the observation/measurement changeover switch 27 is switched to the measurement mode while maintaining the standard/pulser changeover controller 28 selected in the standard mode, the state of the power supply is changed to bring the endoscope to the measuring mode. A constant voltage from the laser beam power supply 23 is supplied to the laser beam power supply 11, and laser beams illuminate the transmission type fiber diffraction grating 12 continuously via the optical fiber 16. Accordingly, only a pattern projection light 13 is projected on the object to be measured, and a distinct matrix-like two-dimensional spot light pattern which is not affected by the illumination light for observation is obtained.

Further, if the standard/pulse changeover controller 28 is switched to the pulse mode, while the system is in the measurement mode, the voltage from the white light power supply 24 is supplied to the white light source 17. Then, the white light source 17 is turned on pulsatively, and a pulse-like illumination light for observation, adjusted to a prescribed repetition cycle by the pulse timing control circuit 26, illuminates the object to be measured, while the pattern projection light 13 is being projected continuously on the object (measurement mode of FIG. 11(b)).

In the illumination mode with pulsative illumination light for observation in the measurement mode, the readout of the spot light pattern generated by the pattern projection light and the image for observation generated by the illumination light for observation is controlled appropriately by a readout clock (FIG. 11(c)) for the solid-state image receiving element 22. Thus, the spot light pattern, for example, is read out in even-field periods of the solid-state image receiving means 22, while the observational image due to illumination light for observation is read out in odd-field periods, with measurements and ordinary observations proceeding in parallel.

Next, each mode of measurement and ordinary observation of an object to be measured which is illuminated with appropriate timings by the pattern projection light and illumination light for observation, will be described.

First, describing the ordinary observation mode, an image of the object to be measured is picked up by the solid-state image receiving element 22 while the object is illuminated by the illumination light for observation, which comes through the illumination lens 22, and is read out, for example, in odd-field periods.

An image signal read out from the solid-state image receiving element 22 is input to the camera control unit 31 from which are obtained through its color processing circuit a luminance signal $E_y$ and color difference signals $E_i$ and $E_q$. These signals are separated in the decoder 32 into R, G, and B color component signals $E_r$, $E_g$, and $E_b$, and after A/D conversion they are recorded as memories 33r, 33g, and 33b, respectively. Then, television signals are output from memories 33r, 33g, and 33b as standard signals of, for example, an NTSC system, to be displayed on the CRT monitor 38 as a color image, enabling ordinary observation of the object to be measured.

On the other hand, in the measurement and observation mode, the luminance signal $E_y$ is sent to the noise processing portion 34 to be subjected to noise processing. The noise processed signal is sent to the binarization processing portion 35 to detect the spot light. First, the luminance signal $E_y$ undergoes a binarization processing in the binarization processing portion 34, in which portions with luminance greater than a reference threshold level $T_h$ are given the classification "1" while portions with smaller luminance than the reference threshold level are given the classification "0". In this way, the sites irradiated by the pattern projection light 13 can be detected, with the sites irradiated by the pattern projection light 13 classified as "1", i.e., as having a higher luminance, and other sites being classified as "0".

Next, the binary processed image signal is subjected to line thinning processing in the line thinning processing portion 36 in order to find the center point of each projected spot, namely, each pixel. The image of the spot light pattern thus obtained has intervals between the spots in the row and column directions which are varied in accordance with the form of the object to be measured.

Figure 12:
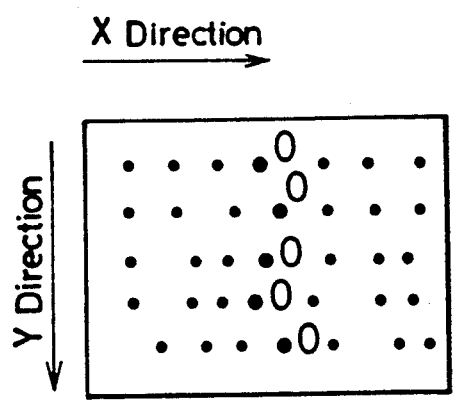
FIG. 12 is a diagram showing an image of the spot light pattern projected on an object to be measured in the measuring endoscope in accordance with the present invention.

First of all, in the pixel coordinate detecting portion 37, the coordinate of the 0-th order term in the X direction, namely, in the parallax direction, is detected using the image of the spot light pattern obtained as shown in FIG. 12. Here, detection of the 0-th order term is carried out according to the method which emphasizes only the 0-th order diffraction light at the center (*Gas-troenterological Endoscopy*, Vol. (25) 6, June, 1983, PP. 868-874).

Figure 14:
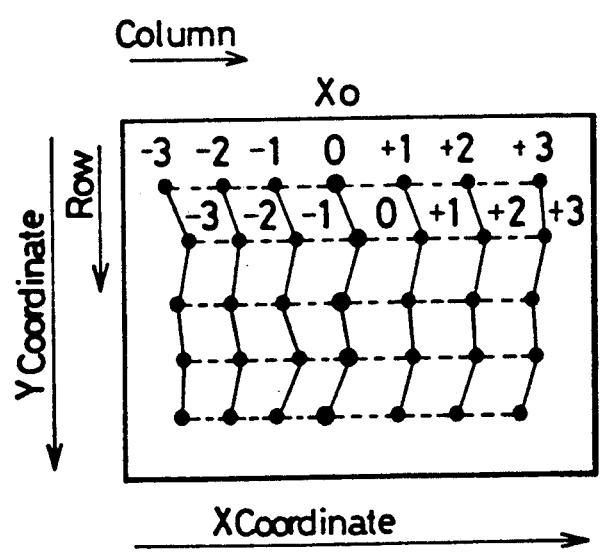
FIG. 14 is a diagram for explaining the addressing of each spot on the image plane.
Figure 13:
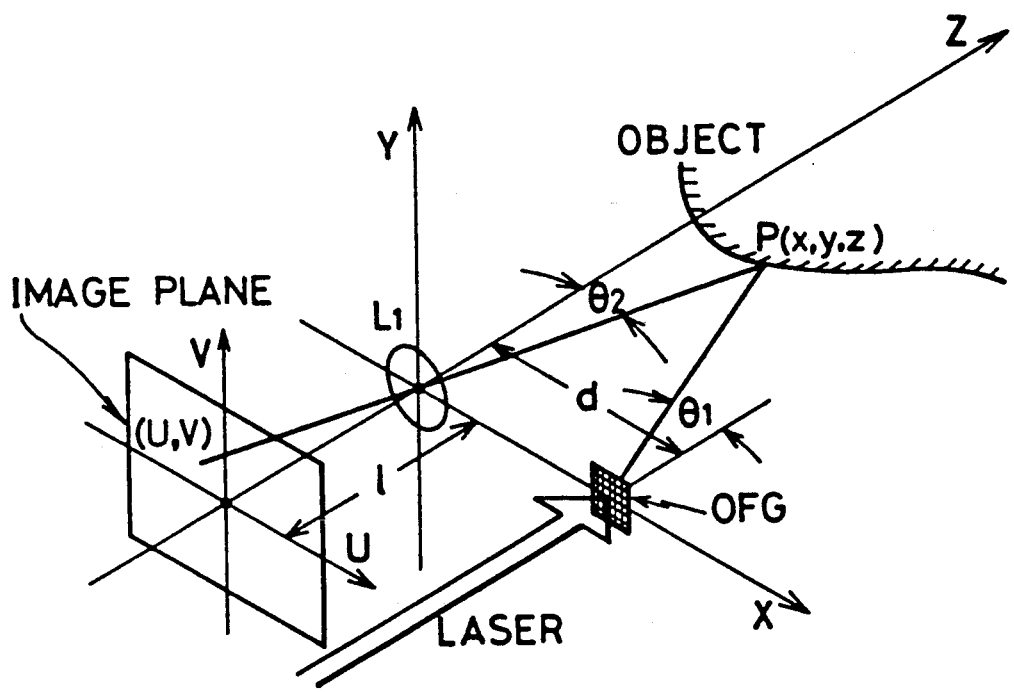
FIG. 13 is a diagram for explaining the method of calculating the reference distance from the surface of the observation system to a reference plane.

Referring to FIG. 13, since the diffraction order of the other spot is determined with the detecting of the 0-th order spot, the coordinate (x, y, z) of the pattern projection light is calculated in the following manner.

$$\theta_1 = \sin^{-1}(h \cdot \lambda / D) \quad (1)$$

$$\theta_2 = \tan^{-1}(u/l) \quad (2)$$

$$Z = a/(\tan\theta_1 + \tan\theta_2)$$

$$x = u/l \cdot Z$$

$$y = v/l \cdot z$$

where
h: diffraction order
λ: wavelength of laser
D: pitch of the diffraction grating In FIG. 14, there is shown an example of a pattern on the image plane shown in FIG. 13.

Furthermore, as a method of calculating the coordinate (x, y, z) by using the coordinate (u, v) on the image plane, there is a method of pre-calculating a geometric field $\theta$ angle X (direction X), $\theta$ angle Y (direction Y) and a center coordinate of the visual field $(U_o, V_o)$ in the following manner.

$$\theta_2 = \frac{(u - u_o)}{\text{pixel number in the } X \text{ direction}} \cdot \theta \text{ angle } x$$

$$x = \tan\theta_2 \cdot Z$$

$$\theta_3 = \frac{(v - v_o)}{\text{pixel number in the } Y \text{ direction}} \cdot \theta \text{ angle } y$$

$$y = \tan\theta_3 \cdot Z$$

Here, for example, λ = 630 nm and D = 25μ,
$\theta_1 = 1.44°$ (1-th order)
$\theta_2 = 2.89°$ (2-th order).

After the distance $Z_h$ has been calculated for the spots of various orders, a displacement curve is prepared with the X coordinate, $X_{hpix}$, on the abscissa and $(Z_h - Z_o)$ on the ordinate. Here, $(Z_h - Z_o)$ represents the displacement of the unevenness from the reference plane 10.

As in the above, the distance $Z_h$ to the spots of various orders and the displacement curve $X_{hpix}$ vs. $(Z_h - Z_o)$ are determined, based on the interval $P_a$ that corresponds to the parallax. The displacement curve $X_{hpix}$ vs. $(Z_h - Z_o)$ is found for the spot array of each row. For pixels with no spots, the displacement is interpolated using the values of the displacements for the spots preceding and succeeding the pixel.

In this manner, the degree of swelling or depression or the like of the object to be measured can be determined from the distance $Z_h$ between the observation point (the point where the solid-state image receiving element is arranged) and the object where a morbid growth exists, or the size of the morbid growth, and the displacement curve.

Next, in FIG. 16 and FIG. 17 there is shown another embodiment of the present invention.

In this embodiment, an irradiation timing control means is constituted by a mechanical means. Namely, between a laser light source 11 and an optical fiber 16 for guiding the laser beams, and a white light source 17 and an optical fiber 18 for guiding illumination light for observation, there are arranged filters (optical choppers) 38 and 39, independently turnable, as a means of mechanical irradiation timing control.

By means of the filter 38, laser beams from the laser light source 11 are converted into pulsed laser beams, as shown in FIG. 17(b), while illumination light for observation from the white light source 17 is converted into pulsed illumination light for observation, as shown in FIG. 17(a). The pulsed laser beams and the pulsed illumination light for observation fall upon the optical fibers 16 and 18, respectively, with alternate timings. Accordingly, the object to be measured is irradiated in an alternating fashion with the pulsating pattern projection light and the pulsating illumination light for observation.

In this embodiment, the processing circuit used for the image signal read out from the solid-state image receiving element is similar to that used in FIG. 8.

Similar to the previous embodiment, a spot light pattern obtained by the pattern projection light is read out, for example, during the even-field period in the solid-state image receiving element, by means of the read out clock of the solid-state image receiving element (FIG. 17(c)), and an image for observation by the illumination light for observation is read out during the odd-field period, achieving measurement and ordinary observation in parallel.

In FIG. 18 is shown a modification of irradiation timings for the pattern projection light (FIG. 18(b)) and the illumination light for observation (FIG. 18(a)) in the above embodiment.

In this variation, by addition of a necessary modification to the constitution of filters 38 and 39, the pulse widths of the pattern projection light and the illumination light for observation are reduced to the full extent possible, and the illumination light for observation is arranged to illuminate the object immediately before the clock for read out of the odd field (FIG. 18(b)) and the pattern projection light irradiating the object immediately after the same readout clock.

With such irradiation timings, it is possible to reduce the error between an ordinary observation and a measurement when a living body or the like, which constitutes the object to be measured, is not stationary.

The modes for the irradiation timings of the pattern projection light and the illumination light for observation, as shown in FIG. 17 and FIG. 18, can also be realized by the use of an irradiation timing control means constituted by an electrical means consisting of an observation measurement changeover switch 27 and the like shown in FIG. 8.

Further, when the object to be measured is nonstationary, it may be so arranged as to irradiate the object simultaneously with the illumination light for observation and the pattern projection light when the object is to be observed as a moving picture during ordinary observation, and switching over to the irradiation timings as shown in FIG. 11 only when the image of the object is to be picked up as a stationary picture.

As described in the foregoing, according to the endoscope of the present invention, it is possible by means of an irradiation timing control means to control the irradiation timings to a necessary mode in which, for example, irradiation is switched between the pattern projection light for measurement and the illumination light for observation. With such an arrangement, a distinct matrix-like two-dimensional spot light pattern which is free from the influence of the illumination light for observation can be obtained on the object to be measured, when making a measurement, and illumination light for observation alone can be used for irradiating the object when an ordinary observation is to be made. In this manner, measurement and ordinary observation can be carried out appropriately.

Next, referring to FIG. 19, the constitution of a pixel coordinate detecting portion 37 (FIG. 8) will be described in detail. The detecting portion 37 is formed by connecting a Y direction profile generating portion 45, which receives the output from a line thinning processing portion 36, to a Y direction center coordinate detecting portion 46, connected sequentially by a column data collection range column detecting portion 47 and an X direction profile generating portion 48. After connecting a spot center coordinate detecting portion 49 and a 0-th order term coordinate detecting portion 50, in parallel, to the output line of the generating portion 48, there are then connected in succesion a spot addressing portion 51, an identical order spot connecting portion 52 as a pinstripe pattern conversion means, and a monitor 53.

A column direction (Y direction) center coordinate detecting means is constituted with the Y direction profile generating portion 45 and the Y direction center coordinate detecting portion 46, and a spot coordinate detecting means is constituted with the column data collection range detecting portion 47, the X direction profile generating portion 48, the spot center coordinate detecting portion 49, the 0-th order term coordinate detecting portion 50, and the spot addressing portion 51.

Figure 20:
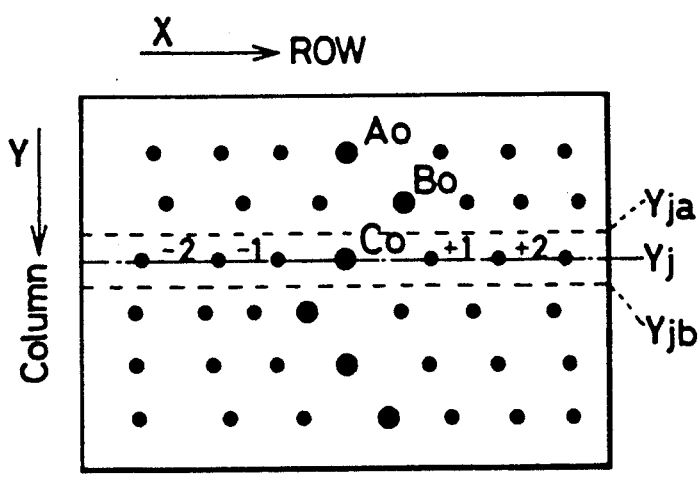
FIG. 20 is a diagram showing an image of a spot light pattern projected onto an object to be inspected.

Next, referring to FIG. 20 and FIG. 21, the action of the endoscope will be described.

First, the scope 19 is inserted to a desired portion of the body where pattern projection light 13 from the transmission type fiber diffraction grating 12 irradiates the object to be measured 14, the and then an image of the object is picked up by the solid-state image receiving element 22.

The image signal output from the solid-state image receiving element 22 is input to the camera control unit 31 where a luminance signal $E_y$ and color difference signals $E_i$ and $E_q$ are obtained by its color process circuit. Of these signals, the luminance signal $E_y$ is guided to a noise processing portion 34 to be noise processed there, and spot detection is carried out in a binarization processing portion 35. In the binarization processing portion 35, binarization processing is performed for the noise processed luminance signal $E_y$ in which portions with luminance higher than a reference threshold level $T_h$ are designated "1", while those portions with lower luminance are designated "0". These areas irradiated by the pattern projection light 13 have a higher luminance, so they are classified as "1", and other areas are classified as "0", for the purpose of spot detection.

Next, the image signal which went through binarization processing is subjected to line thinning processing in the line thinning processing portion 36 to determine the center position of each spot of the pattern projection light 13, namely, each pixel. In the image of the obtained spot light pattern, the spot intervals only in the direction of parallax, namely, the X direction, are varied in accordance with the form of the object to be measured, as shown in FIG. 20, without any change in the coordinates in the Y direction. In the Y direction profile generating portion 45 of the pixel coordinate detecting portion 37, a profile in the Y direction is generated from the image of the spot light pattern in the following manner, as shown in FIG. 21.

Namely, if it is assumed that the pixel size of a screen for the spot light pattern is 512×512, for example, and that the luminance data or data which binarizes the luminance data of each pixel is called $I_{ij}$ (i=1-512 and j=1-512), the profile in the Y direction is generated by summing all of these data in the X direction for each column:

$$\sum_{i=1}^{512} I_{ij}(j)$$

In the Y direction center coordinate detecting portion 46, binarization is applied to the profile obtained as above with respect to a prescribed threshold $T_{h1}$, and by detecting its center coordinates the center coordinates $Y_1, Y_2, \ldots, Y_n$ are determined for each spot column.

Next, in the column data collection range detecting portion 47 or in the spot address assigning portion 51, the number of the diffraction order (referred to as order number or order term hereinafter) is determined for the spots $Y_1, Y_2, \ldots, Y_n$ for each column obtained as above.

Namely, first, in the column data collection range detecting portion 47, the range $Y_{ja}$ and $Y_{bj}$, which accommodate the data for each column, is determined from the data for the center coordinates $Y_1, Y_2, \ldots, Y_n$ for each column.

Figure 21:
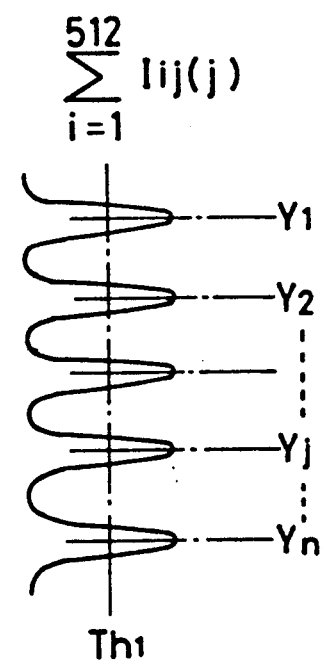
FIG. 21 is a diagram showing the center coordinate in the X direction and the profile in the column direction of spots obtained from the spot light pattern in FIG. 20.
Figure 22:
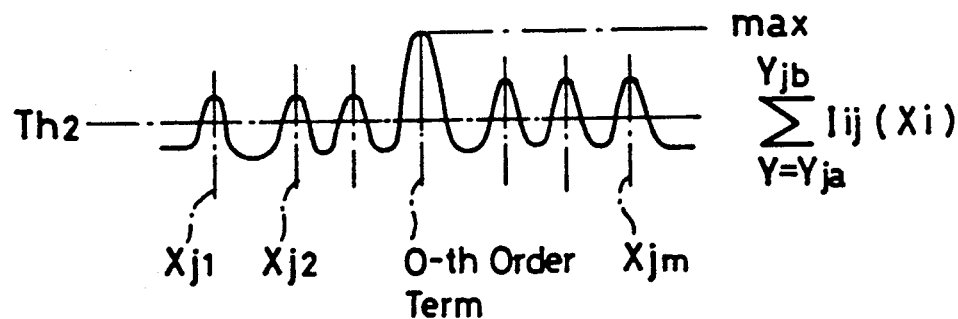
FIG. 22 is a diagram showing the spot coordinate in the Y direction and the profile in the row direction of spots obtained from the spot light pattern in FIG. 21.

In X direction profile generating portion 48, the luminance data $I_{ij}$ for each pixel is summed in the Y direction within the range $Y_{ja}$ and $Y_{jb}$, written as $$\sum_{Y=Y_{ja}}^{Y_{jb}} I_{ij}(X_i),$$

to generate the profile in the X direction for each column (FIG. 21).

In the spot center coordinate detecting portion 49, binarization is applied to the above profile with respect to a prescribed threshold level $T_{h2}$, and from its center coordinate the center coordinates for each column are determined.

In the 0-th order term coordinate detecting portion 50, the coordinates of the 0-th order terms $A_0, B_0, C_0, \ldots$ are detected from among the maximum X coordinates in the X direction profiles. The coordinate detection of the 0-th order term is carried out by the publicized method (*Gastroenterological Endoscopy*, Vol. (25) 6, June, 1983, PP 868-874) which emphasizes only the diffracted light of the 0-th order term by the use of the transmission type fiber diffraction grating 12.

In the spot address assigning portion 51, address assignments, namely, allocation of the order of diffraction, are carried out for spots in each column, with the spot coordinate of the 0-th order term as the center. Allocation of the diffraction order is carried out by giving the order numbers $-1, -2, \ldots$ successively in the descreasing order of the coordinates starting with the 0-th order term, and the order numbers $+1, +2, \ldots$ in the increasing order of the coordinates. The above operation of address assigning is carried out for $Y_1, Y_2, \ldots, Y_n$ for each column, to determine the order numbers for all the spots.

Figure 23:
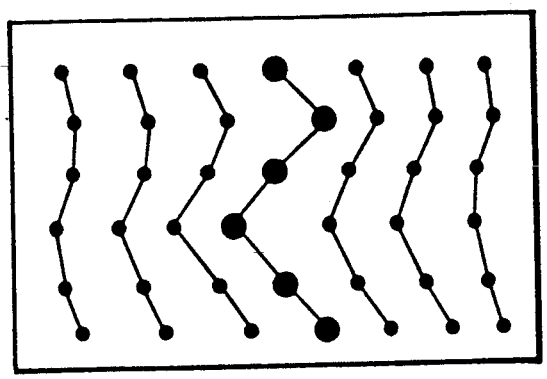
FIG. 23 is a diagram showing a converted pinstripe pattern.

After address assignment has been completed for all the spots, they are then connected in the identical order spot connecting portion 52 by carrying out interpolation between spots with the same order in each column $Y_1, Y_2, \ldots, Y_n$, to obtain a vertical stripe pattern as shown in FIG. 23.

The image of the stripe pattern is displayed distinctly on the monitor 53, as well as the unevenness existing on the object to be inspected from the stripe pattern.

As described in the foregoing, according to the endoscope using the above coordinate detecting portion, the transmission type diffraction grating and the image receiving means are mounted with prescribed intervals so as to generate a parallax only in a direction the same as the row direction of the spot light pattern. The intervals between the spots in each column of the spot light pattern, of the image picked up by the image receiving means, are varied due to the parallax in response to the form of the object to be inspected. Interpolation is applied, spots with the same diffraction order in each column are connected, and unevenness information on the object to be inspected is obtained as a distinct stripe pattern. Therefore, there is an advantage in that the unevenness existing on the object to be inspected can be recognized easily and accurately.

Figure 24:
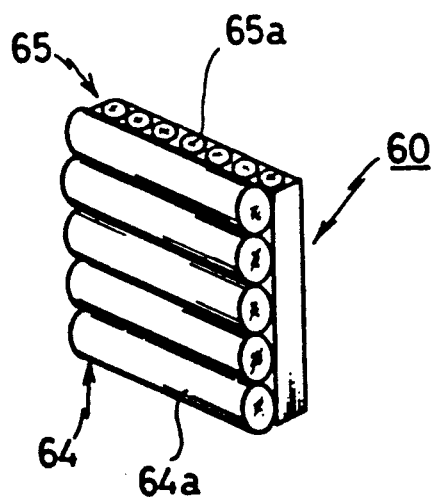
FIG. 24 is a perspective view of another transmission type diffraction grating of the measuring endoscope in accordance with the present invention.

In addition, in the above embodiment, more effective observation and measurement are possible by changing the constitution of the grating 12. FIG. 24 shows one of such examples. In this case, a two-dimensional transmission type diffraction grating 60 is constituted by a first one-dimensional fiber diffraction grating 64 and a second one-dimensional fiber diffraction grating 65, placed on the first diffraction grating 64 and having a diffraction angle that is different from that of the first one-dimensional fiber diffraction grating, for diffracting the light diffracted by the first one-dimensional fiber diffraction grating 64 in the row-direction.

For glass fibers 64a constituting the first one-dimensional fiber diffraction grating 64, use is made of fibers having diameters of about 100 μm, for example, and for glass fibers 65a constituting the second one-dimensional glass fiber diffraction grating 65, use is made of fibers having diameters of about 10 μm, for example.

Here, it is noted that there exists the following relation $$\phi_h = \sin^{-1}(h \cdot \lambda/D) \quad (7)$$

between the diffraction angle $\phi_h$ of the one-dimensional fiber diffraction grating and the diameter D of the glass fiber constituting the one-dimensional fiber diffraction grating.

In the above equation
h: order of diffracted light $(0, +1, +2, \ldots)$
λ: wavelength of the incident laser light.

From Eq.(7) it is seen that the diffraction angle $\phi_h$ of the one-dimensional fiber diffraction grating decreases with an increase in the diameter D of the glass fiber which constitutes the grating. Thus, for example, for λ=488 nm, in the case of the first one-dimensional fiber diffraction grating 64 that uses glass fibers 64a with diameters of 100 μm, the diffraction angle is 0.28°, and in the case of the second one-dimensional fiber diffraction grating 65 that uses glass fibers 65a with diameters of 10 μm, the diffraction angle $\phi_h$ is 2.75°.

As in the above, the first one-dimensional fiber diffraction grating 64 and the second one-dimensional fiber diffraction grating 65 are set to have different diffraction angles $\phi_h$ by using glass fibers with different diameters for these gratings.

Since the measuring endoscope of the present embodiment is constituted as in the above, when laser beams from the laser light source 11 are incident on the transmission type diffraction grating 60, the laser beams are diffracted one-dimensionally in the column direction with a diffraction angle, for example, of 0.28° by the first one-dimensional fiber diffraction grating 64. These diffracted beams are then diffracted in the row direction with a diffraction angle of, for example, 2.75° by the second one-dimensional fiber diffraction grating 65. As a result, on the object to be inspected there is projected a two-dimensional spot light pattern which approximates a pinstripe pattern in which the intervals between the spots in the column direction are contracted.

Figure 25:
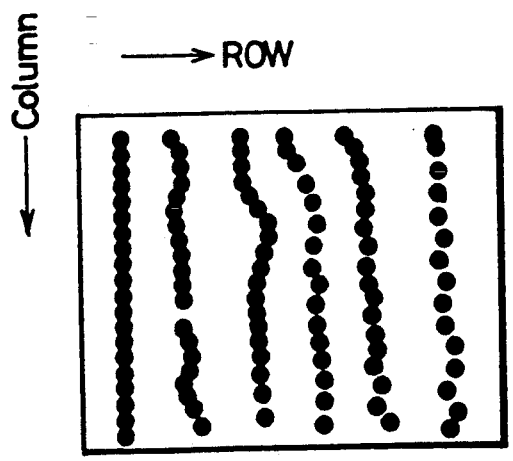
FIG. 25 is a diagram showing a pattern approximating a pinstripe pattern picked up by the image receiving means of the measuring endoscope in accordance with the present invention.

FIG. 25 shows the image of such a spot light pattern picked up by the solid-state image receiving element which displays a clear image of a spot light pattern that approximates a pinstripe pattern with variations in the intervals between the spots in response to the form of the object to be inspected. In this manner, unevenness or the like existing on the object to be inspected can be recognized easily and accurately from the pattern which approximates a pinstripe pattern displayed clearly on the monitor.

Figure 26:
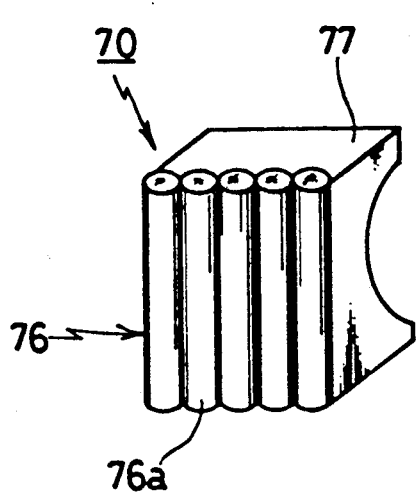
FIG. 26 is a perspective view showing still another transmission type diffraction grating.
Figure 27:
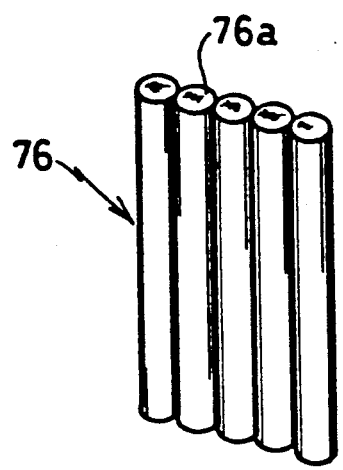
FIG. 27 is a perspective view showing the one-dimensional fiber diffraction grating in the transmission type diffraction grating shown in FIG. 26.

Next, in FIG. 26 and FIG. 27 there is shown a two-dimensional transmission type diffraction grating that is different from the embodiment in the above.

This transmission type diffraction grating 70 is constructed by overlapping a one-dimensional fiber diffraction grating 76 for diffracting the laser beams in the row direction and a cylindrical concave lens 77 for enlarging the light diffracted by the one-dimensional fiber diffraction grating 76 in the column direction. As glass fibers 76a constituting the one-dimensional fiber diffraction grating 76, use is made of fibers having diameters smaller than about 20–50 μm in order to generate a plurality of spot lights in the column direction.

Figure 28:
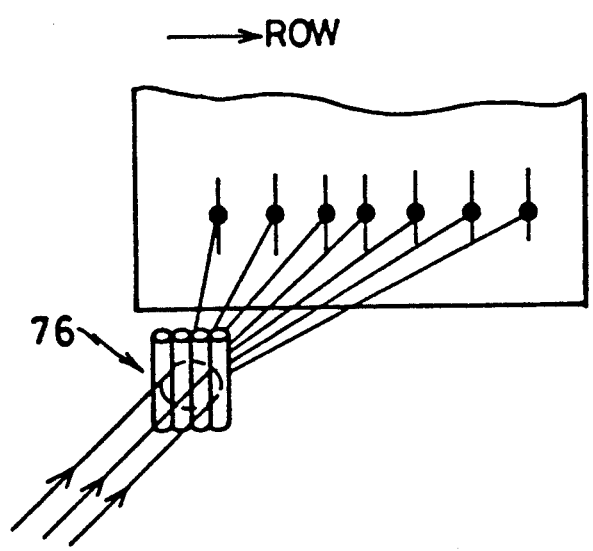
FIG. 28 is a perspective view showing diffraction action of the one-dimensional fiber diffraction grating of FIG. 26.

Since the measuring endoscope of this embodiment is constructed as in the above by a use of a transmission type diffraction grating 70, when laser beams from the laser light source 11 are incident on the transmission type diffraction grating 70, the laser beams are diffracted first one-dimensionally by the one-dimensional fiber diffraction grating 76, as shown in FIG. 28. The diffracted beams are then enlarged in the column direction by the cylindrical concave lens 77, to project a clear pinstripe pattern on the object to be inspected.

Next, image signals of the pinstripe pattern with changes in response to the form of the object to be inspected are obtained from the solid-state image receiving element, and from the pinstripe pattern which is displayed clearly on the monitor (CRT), unevenness or the like existing on the object to be inspected can be recognized easily and clearly.

Figure 29:
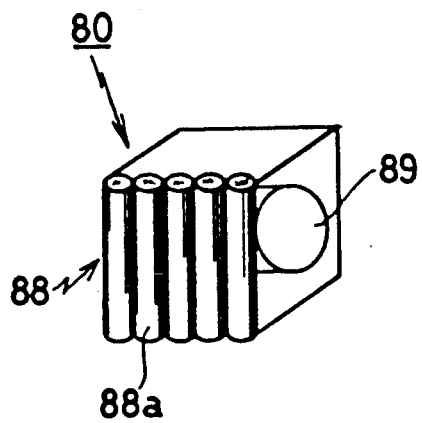
FIG. 29 is a perspective diagram showing still another transmission type diffraction grating.
Figure 30:
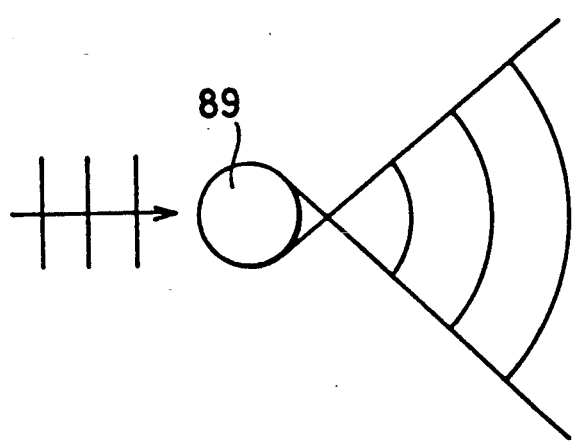
FIG. 30 is a diagram showing the enlarging action in the column direction by a cylindrical lens in the transmission type diffraction grating of FIG. 29.

Referring to FIGS. 29 and 30, there is shown still another two-dimensional transmission type diffraction grating which can be applied to the present embodiment.

A transmission type diffraction grating 80 is constituted by overlapping a one-dimensional fiber diffraction grating 88 which diffracts laser beams in the row direction and a cylindrical lens 89 which enlarges the beams diffracted in the column direction by the one-dimensional fiber diffraction grating 88. For glass fibers 88a constituting the one-dimensional fiber diffraction grating 88, use is made of a glass fibers with diameters comparable to that used in the previous example.

Since this measuring endoscope is constructed using the transmission type diffraction grating 80 described above, upon incidence of laser beams on the transmission type diffraction grating 80, the laser beams are diffracted one-dimensionally in the row direction by the one-dimensional fiber diffraction grating 88, analogously to the case of FIG. 28. The diffracted beams are then enlarged in the column direction by the cylindrical lens 89, and a clear stripe pattern similar to the previous case is projected on the object to be inspected.

Figure 31:
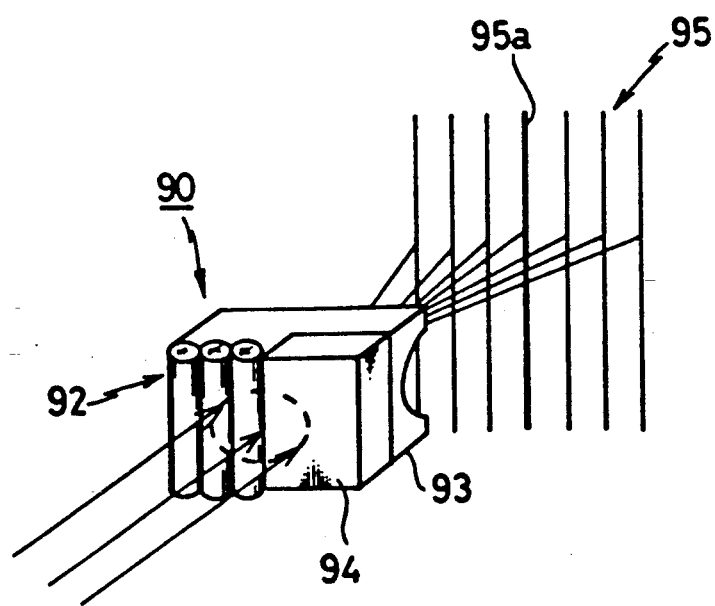
FIG. 31 is a perspective view showing still another transmission type diffraction grating.

In FIG. 31 there is shown a still another example of the two-dimensional transmission type diffraction grating.

A transmission type diffraction grating 90 of this embodiment has a basic constitution which is approximately similar to the previous example (FIG. 26) in which a one-dimensional fiber diffraction grating 92 which diffracts laser beams in the row direction is overlapped on a cylindrical concave lens 93 which enlarges in the column direction the beams diffracted by the one-dimensional fiber diffraction grating 92. In addition to such a basic constitution, the transmission type diffraction grating 90 of this embodiment has a transparent plate 94 which occupies approximately one half of the front side on which is arranged the one-dimensional fiber diffraction grating 92.

Since the transmission type diffraction grating 90 of this embodiment is constituted as in the above, a pinstripe pattern 95 is projected on the object to be inspected, analogous to the previous case, due to the diffracting action in the row and column directions of the one-dimensional fiber diffraction grating 92 and the cylindrical concave lens 93. Moreover, detection of the coordinate of a 0-th order stripe 95a is facilitated by the emphasis on the brightness of the stripe 95a of 0-th order fringe brought about by the presence of the boundary between the one-dimensional fiber diffraction grating 92 and a transparent plate 94. The detection of the coordinate of the 0-th order fringe 95a is needed in the determination of the distance from the plane of observation to the spot (fringe) of various orders.

As described above, a two-dimensional transmission type diffraction grating of the constitution as in the above is constructed by overlapping a one dimensional fiber diffraction grating which diffracts laser beam in either one of the row or column directions, and another one-dimensional fiber diffraction grating or a lens body, having a diffraction angle different from that of the one-dimensional fiber diffraction grating just described, which diffracts or enlarges the beams diffracted by the first one-dimensional fiber diffraction grating in the other of the row or column directions. Therefore, in the diffracted two-dimensional spot light, intervals between the spots are contracted or made continuous in either one of the row or column directions. Thus, unevenness information obtained from the object to be inspected is in a pinstripe pattern or a clear pattern which approximates a pinstripe pattern. Therefore, there is obtained an advantage in that unevenness or the like existing on the object to be inspected can be recognized easily and clearly.

Various modifications will become possible for those skilled in the art after receiving the instructions of the present disclosure without departing from the scope thereof.

What is claimed is:

1. An endoscope for measuring the form of an inaccessibly situated object, comprising:
    a fiber having an inner end to be located near said object and an outer end to be situated remote from said object, the fiber transmitting geometrical information of said object from said inner end to said outer end of said fiber;
    a diffraction grate provided at the inner end of said fiber;
    a laser beam source connected to said fiber, in order to transmit a laser beam through said diffraction great to diffract the laser beam and project a diffracted pattern of said laser beam onto a surface of said object;
    image pickup means provided at the inner end of said fiber for receiving the laser beam in the form of said pattern reflected by a surface of said object to obtain the geometrical information of said surface for transmission to the outer end through said fiber; and
    visualizing means connected to the outer end of said fiber for visualizing means connected to the outer end of said fiber for visualizing the geometrical information transmitted to the outer end;
    wherein said grate comprises two grating parts for carrying out diffraction in mutually orthogonal first and second directions, the respective grate parts having different diffraction angles.

2. The endoscope of claim 1 wherein said fiber is an optical glass fiber through which said laser beam is transmitted from the inner end to the outer end.

3. The endoscope of claim 2 further comprising a white light source connected to said fiber, in order to transmit a white light onto the surface of said object.

4. The endoscope of claim 1 wherein said image pickup means is an image sensor for converting optical information from said pattern into equivalent electrical signals.

5. The endoscope of claim 4 wherein said image sensor is a CCD.

6. The endoscope of claim 1 wherein said visualizing means comprises a decoder provided with a display for converting electrical signals into visual information of the original pattern.

7. An endoscope for measuring the form of an inaccessibly situated object, comprising:
    a fiber having an inner end to be located near said object and an outer end to be situated remote from said object, said fiber transmitting geometrical information of said object from said inner end to said outer end of said fiber;
    a diffraction grate provided at the inner end of said fiber;
    a cylindrical lens provided at the inner end of said fiber and overlapped around said diffraction grate such that an axis of said cylindrical lens is directed perpendicularly to the diffraction direction of said diffraction grate;
    a laser beam source connected to said fiber in order to transmit a laser beam through said diffraction grate to diffract the laser beam and project a diffracted pattern of said laser beam onto a surface of said object;
    image pickup means provided at the inner end of said fiber for receiving the laser beam in the form of said pattern reflected by said surface, to obtain the geometrical information of a surface of said object, to be transmitted to the outer end through said fiber; and
    visualizing means connected to the outer end of said fiber for visualizing the geometrical information transmitted to the outer end.

8. An endoscope for measuring the form of an inaccessibly situated object, comprising:
    a fiber having an inner end to be located near said object and an outer end to be situated remote from said object, for transmitting geometrical information of the form of said object from said inner end to said outer end of said fiber;
    a pair of mutually overlapped diffraction grated provided at the inner end of said fiber, said grates having mutually perpendicular diffraction directions;
    a laser beam source connected to said fiber in order to transmit a laser beam through said diffraction grate to diffract the laser beam and project a diffraction pattern in the form of diffraction spots of said laser beam to a surface of said object;
    image pickup means provided at the inner end of said fiber for receiving the laser beam in the form of said pattern reflected by said surface to obtain the geometrical information of said surface to be transmitted to the outer end through said fiber; and
    visualizing means connected to the outer end of said fiber for visualizing the geometrical information transmitted to the outer end;
    herein said visualizing means displays the diffraction spots in identical diffraction order, with respect to the direction which connects the pair of said diffraction grates and said image pickup means, represented as a continuous line, by carrying out interpolation between the spots.

* * * * *